United States Patent [19]

Kleehammer

[11] Patent Number: 5,583,765
[45] Date of Patent: Dec. 10, 1996

[54] REMOTE SYSTEM FOR MONITORING THE WEIGHT AND EMISSION COMPLIANCE OF TRUCKS AND OTHER VEHICLES

[75] Inventor: Robert Kleehammer, Huntington, N.Y.

[73] Assignee: Grumman Aerospace Corporation, Los Angeles

[21] Appl. No.: 294,356

[22] Filed: Aug. 23, 1994

[51] Int. Cl.$^6$ ............................ G01J 3/443; G01N 21/00
[52] U.S. Cl. .................. 364/423.098; 250/338.5; 250/339.04; 250/339.07; 364/567
[58] Field of Search ................... 364/424.01, 424.04, 364/436, 496, 497, 498, 499, 431.06, 463, 466, 567; 73/117; 340/440; 250/338.5, 339.04, 339.07; 123/357; 177/136

[56] References Cited

U.S. PATENT DOCUMENTS

| | | | |
|---|---|---|---|
| 3,630,072 | 12/1971 | Traver | 73/23 |
| 4,680,959 | 7/1987 | Henry et al. | 73/117 |
| 4,812,806 | 3/1989 | Freeman | 340/440 |
| 4,924,095 | 5/1990 | Swanson, Jr. | 250/338.5 |
| 5,210,702 | 5/1993 | Bishop et al. | 364/496 |
| 5,315,977 | 5/1994 | Fosseen | 123/357 |
| 5,394,327 | 2/1995 | Simon, Jr. et al. | 364/424.01 |
| 5,416,711 | 5/1995 | Gran et al. | 364/436 |
| 5,442,553 | 8/1995 | Parrillo | 364/424.04 |

Primary Examiner—Gary Chin
Assistant Examiner—Russell W. Frejd
Attorney, Agent, or Firm—Terry J. Anderson; Karl J. Hoch, Jr.

[57] ABSTRACT

A remote non-contacting vehicle load and emissions compliance monitoring system includes a remote vehicle velocity detector, a remote emissions temperature sensor, a remote emissions content monitor, and a processing and computing unit connected to receive data from the sensors and compute the vehicle load based on the vehicle velocity and emissions temperature, as well as on road and environmental conditions and stored vehicle operating specifications, and to compare the observed exhaust plume content with a model emissions profile based on the computed load and vehicle characteristics.

44 Claims, 1 Drawing Sheet

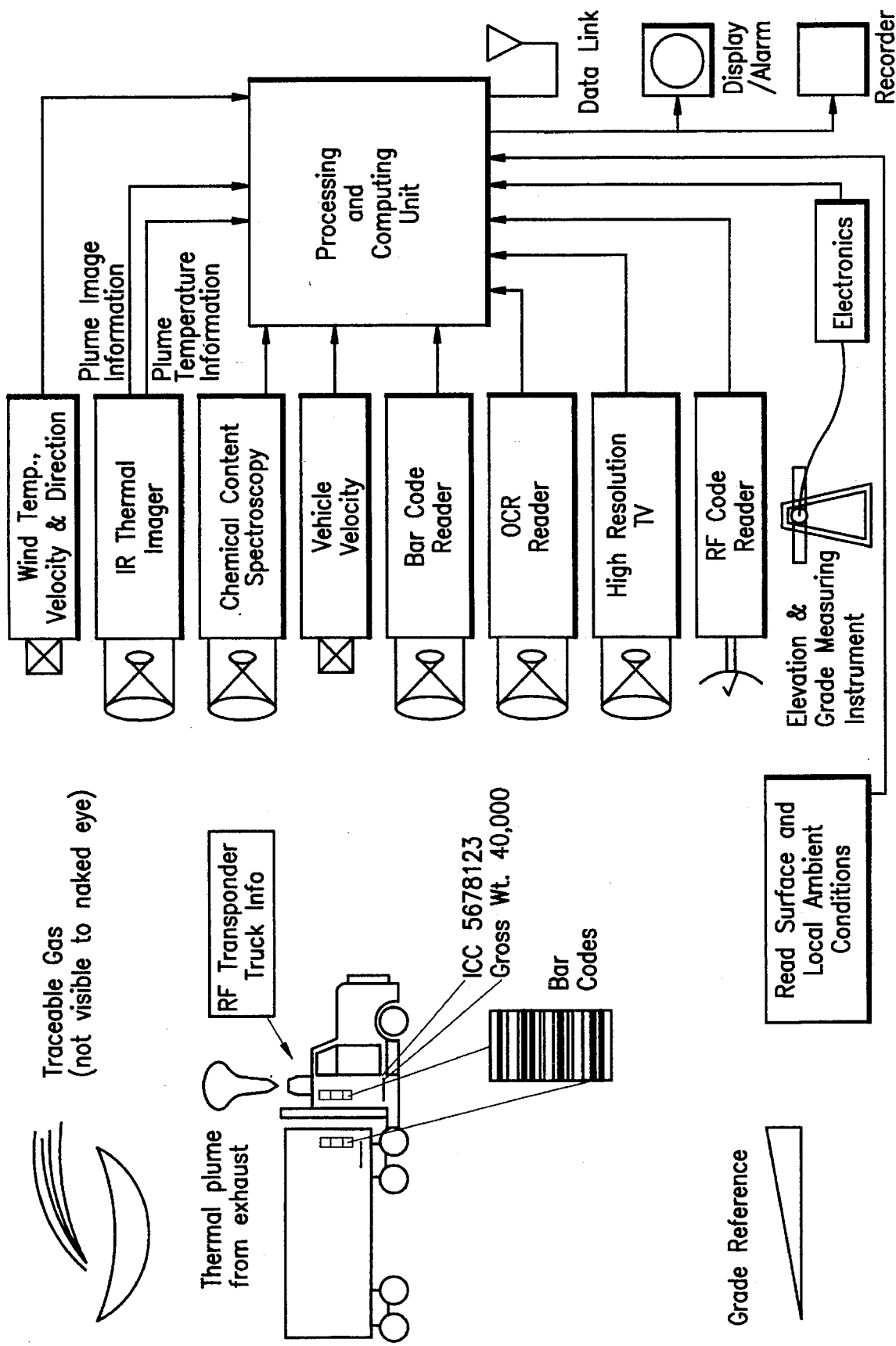

REMOTE SYSTEM FOR MONITORING THE WEIGHT AND EMISSION COMPLIANCE OF TRUCKS AND OTHER VEHICLES

BACKGROUND OF THE INVENTION

1. Field of the Invention

This invention relates to apparatus and a method for enabling computation and display of information by remote measurements, and in particular to apparatus and a method for remotely determining vehicle weight and emission compliance.

2. Description of Related Art

In order to maintain highway infrastructure, assess taxes and fees, and keep vehicle generated pollution to a minimum, all states have developed programs for measuring the weight and emission compliance of trucks and other vehicles. Initially, such programs involved testing the vehicle at off-road weighing and emission compliance monitoring stations. More recently, pressure sensitive strips laid on or in the roadway have been used for weight monitoring.

Both off-road testing and the use of pressure sensitive strips have a number of disadvantages. Off-road testing is a costly procedure for the state and the vehicle operator, while pressure sensitive strips are subject to a high rate of wear and failure due to traffic and weather. Because conventional emission compliance tests are open loop procedures which do not take into account actual operating conditions, such as the load being carried, the conventional tests provide only limited information on the actual pollution costs of a particular vehicle.

SUMMARY OF THE INVENTION

It is accordingly an objective of the invention to provide an apparatus and method for remotely monitoring the weight of trucks and other vehicles which does not require any off-road weighing station or pressure sensitive strips laid on or in the roadway.

It is also an objective of the invention to replace conventional off-road emission compliance stations with an apparatus and method for remotely monitoring the emission compliance of trucks and other vehicles under actual operating conditions.

It is a further objective of the invention to provide a remote monitoring apparatus and method for remotely monitoring both the weight and emissions compliance of vehicles and which has the ability to monitor multiple performance parameters that will provide information on pollution as a function of vehicle load.

It is yet another objective of the invention to provide a real-time closed loop system for measuring pollution-related parameters of a vehicle's performance.

These objectives are accomplished by integrating a variety of new and existing sensor techniques to obtain a remote non-contact system for monitoring both vehicle weight and emission compliance, thereby enabling pollution to be evaluated as a function of load. As a result, the invention provides a more accurate measurement of a vehicle's compliance than is obtained by open-loop pollution measurements in which in which the vehicle is not moving and the effect of load on emissions cannot be taken into account.

In a preferred embodiment of the invention, the remote non-contacting vehicle load and emissions compliance monitoring system includes a remote vehicle velocity detector, a remote emissions temperature monitor or sensor, a remote emissions content monitor, and a processing and computing unit for computing the vehicle load based the vehicle velocity and emissions temperature, as well as road and environmental conditions and stored vehicle operating specifications, and for comparing observed exhaust plume content with a model emissions profile based on the computed load and vehicle characteristics.

In order to identify the vehicle, and thereby enable recall of vehicle operating characteristics from memory, the preferred apparatus includes either a radio frequency (RF) or bar code/optical code reader. Road and environmental data used in the load calculation can be obtained by conventional surveying and meteorological equipment and preferably includes road conditions, grade and elevation, temperature, and wind velocity. Exhaust temperature is preferably detected by an infrared (IR) thermal imager and exhaust content is preferably measured by chemical content spectroscopy. The preferred apparatus also includes displays and alarms for alerting authorities to non-compliant vehicles, and means for recording collected data.

For given conditions, the higher the vehicle weight, the larger the work that must be expended to achieve the same or greater vehicle velocity on a given grade with a given vehicle. According to well-known physical principles, the work expended by the vehicle, W, is given by the equation $W=\frac{1}{2}m(v_f-v_i)^2-mgh\sin\Theta$, where m is the mass of the vehicle, $v_f$ is the final measured velocity, $v_i$ is the initial measured velocity, g is the gravitational acceleration constant, h is the distance travelled, and $\Theta$ is the average grade). The higher the engine work expended, the higher the engine exhaust temperature T, i.e., T=f(W), where f is a function which depends on the engine and gear box operating characteristics. Those skilled in the art will appreciate that visible particulates, as opposed to exhaust temperature, are not a good determinant of work being expended because an engine rich condition, which will cause a large particulate output, may be the result of an engine needing maintenance and is not directly related to total work expended.

While it is well-known that as work increases, temperature increases, conventional exhaust temperature measurements are made with thermocouples and direct reading measurements. The present system allows remote measurement of the expended energy, and by non-contact methods, using an infrared measurement of exhaust heat as the basis for calculation of total expended energy, and consequently the vehicle weight. This information is then used to develop an acceptable emissions profile based on the calculated load, which is compared with actual emissions content information obtained by remote sensors using chemical content spectroscopy.

The preferred method of implementing the remote non-contacting vehicle load and emission compliance monitoring system involves the steps of identifying the vehicle, monitoring vehicle speed and exhaust plume temperature as the vehicle travels up a grade, and then computing the vehicle weight or load based on the measured temperature and velocity, as well as stored vehicle operating characteristics, grade, elevation, road condition data, wind velocity and temperature. The preferred method also includes the steps of measuring exhaust plume content, comparing the exhaust plume content with a profile or model derived from the load and vehicle information, and taking appropriate action such as recording the measured and computed data together with vehicle identification information, with provision for alerting authorities if necessary.

BRIEF DESCRIPTION OF THE DRAWING

The FIGURE is a block diagram of a preferred vehicle weight and emission compliance monitoring apparatus which implements the principles of the invention.

DETAILED DESCRIPTION OF THE PREFERRED EMBODIMENTS

FIG. 1 is a block diagram of the overall system showing a sensor suite and parameters measured. The system provides apparatus and a method for the real time gathering and processing of performance data which results in the determination of vehicle weight and the level of pollutants produced. The real time computations which result in the determination of vehicle weight and pollutants produced are based upon processing data collected from an array of active and passive sensors associated with the system.

Those skilled in the art will appreciate that, while all of the measuring instruments and detectors, monitors, or sensors used by the preferred system are conventional and readily available (and/or implementable) by the skilled artisan, the combination of instruments and techniques used by the preferred system is unique, in particular the real-time remote measurements of vehicle velocity and exhaust plume temperature and content, as well as the inclusion of provision for identifying the vehicle and recalling from memory vehicle operating characteristics and models of acceptable emissions for the measured vehicle behavior. The calculations required to process the measurement information will also be easily implemented by those skilled in the art, using well-known equations which may be varied as conditions dictate, and no attempt is make herein to preempt those formulas.

1. Measuring Instruments and Data Tpyes

The measurement apparatus, which can be fixed base terrestrial, mobile, or airborne, collects a plurality of information data types by use of independent non-contact measuring instruments spanning various spectral bands and techniques. Information data types include:

1) vehicle certification information, obtained by reading a bar code I on the vehicle being tested using a optical code reader (OCR) 2 or other bar code reader, or by receiving RF coded information sent by a transponder 4 on the vehicle 5 in response to an interrogation signal from a base transponder or RF code reader 6,
2) vehicle speed along the road, measured by a radar or laser system 7,
3) ambient conditions, including temperature, wind velocity, and possibly humidity or dew point conditions and/or atmospheric particulate levels measured by conventional meteorological equipment 8,
4) exhaust plume temperature, preferably obtained by an infrared (IR) thermal imager 9,
5) exhaust plume image information, also obtained by the IR thermal imager 9,
6) grade and length or elevation of a section of road, obtained by GPS, prestored survey data, or the like (represented in FIG. 1 by a surveying instrument 10 and interface 11), and ambient road conditions such as the condition of the road surface, and ice or snow coverage measured by conventional sensors 12 and/or obtained from a database,
7) chemical constituents of the exhaust, preferably detected by a chemical content spectrometer 13, and
8) an electro-optical high resolution image of the vehicle captured by a video camera 14 for visual verification.

2. Vehicle Weight or Load Measurement

The vehicle weight or load is measured by observing the effort required by the vehicle in order to maintain speed or accelerate under predetermined or measured conditions. This effort is reflected in the temperature of the exhaust plume and by speed changes during the observation period.

The measurement system is preferably set up by the side of the road in a region where there is an upgrade 16, in order to provide the conditions under which effort must be exerted in order to maintain speed or accelerate. The grade need not have a significant rise, but should have a reasonable length. The object is to cause the engine of a subject vehicle 5 to exert more than the effort required to maintain a constant vehicle speed. Under this condition, the vehicle 5 is constrained to be either attempting to accelerate or to maintain speed up-grade.

The weight of the vehicle, and therefore its load, are measured by taking into account the rise and the distance of the grade, as well as the wind velocity (direction and speed) and other factors which might affect the dynamic behavior of the vehicle, and combining these factors with the observed vehicle velocity and exhaust plume temperature in order to measure the effort or work expended in maintaining the observed speed and/or acceleration. This effort is related to the measured behavior by well-known equations for work as a function of velocity, mass, and distance (such as the work equation $W=\frac{1}{2}m(v_f-v_i)^2-mgh\sin\Theta$, described above). Although the system is most conveniently applied with in situ grade and length measuring instruments such as, for example a GPS transponder system or conventional surveying equipment 10 connected to the appropriate interface 11, so that it can be set up in a variety of different locations, survey information stored in a database could also be used at least with respect to grade and length.

In addition to detecting the exhaust temperature and monitoring vehicle speed, the system takes into account factors such as gearbox and engine specifications which affect the work output of the vehicle. These factors are recalled from a database based on an identification of the vehicle 5 under test. Identification of the subject vehicle 5 is preferably accomplished by remote detection methods involving OCR 2 or bar code reader 3 for reading the coded decal 1 on the vehicle, or an RF code reader 6 for reading information from RF transponder 4 installed on the vehicle. The bar code and/or RF transponder preferably contains information on engine type, gear-box type and/or drive train information, ICC identification number, and gross vehicle weight rating (GVWR). Other information which may be relevant includes license plate registration information. The bar-code 1 or a memory in the RF transponder 4 also preferably contains information on exhaust system configuration and outlet location, including horizontal and vertical orientation so that the exhaust plume can be located by thermal imager 9 and chemical content spectrometer 13.

Each of the measuring instruments in the system is connected to a processing and computing unit 15 which includes a database for storing templates characterizing the vehicle structure in order to identify the general location of the exhaust outlet on the vehicle for measurement. The bar-code decal 1 or transponder 4 is applied to the subject vehicle 5 either upon manufacture, or at a state approved agency, and the transponder is interrogated or the bar code monitored while the truck is the monitored area, i.e., travelling on the grade. The normal operating characteristics of the engine class and gear box combination identified on the vehicle bar-code or stored in the transponder may have been previously gathered either from the truck manufacturer or by testing, and is stored in the processing and computing system database together with routine measurements made by manufacturers during engine development in order to provide a basis for evaluating the engine performance. The known engine and gear box operating characteristics as well as the measurement system parameters, wind velocity, and road grade information are integrated with exhaust temperature measurements obtained from IR thermal imager 9 to determine the amount of work being expended by the engine.

The infrared measurement system represented by thermal imager 9 collects data on the temperature profile of the exhaust plume emitted by the engine. Image processing techniques are employed to segregate the vehicle hard body image from the region of the exhaust plume, and the total actual energy of the engine exhaust is computed from the temperature profile, taking into account the associated ambient conditions such as wind velocity and road conditions which affect the work expended, or temperature which may affect the thermal image.

This information, when adjusted by standard losses due to friction, and the known characteristics of the engine contained in the measurement system database, can be used to compute gross vehicle weight. As a result, a pass-fail determination of vehicle weight status can be computed by processing and computing system 15 based upon the sensor information provided by the remote measurement system.

3. Emissions Content Analysis

At the same time as the vehicle load is being determined based on the work expended in maintaining speed or accelerating on grade 16, represented by the exhaust plume temperature with adjustments for vehicle characteristics and ambient conditions, the vehicle exhaust is analyzed for compliance with emission standards by remote optical spectroscopy or an equivalent optical technique. The measurement system identifies the gaseous and particulate components of the vehicle exhaust to determine compliance with federal and state emission requirements for gasoline/multiple-fuel engines, diesel engines, electric and/or hybrid electric/combustion engines, and any other engine types which might emit particles or gases capable of being detected by spectroscopy or equivalent techniques. Although the exhaust gas particulate concentration which can be measured by existing techniques is not necessarily a precise indication of the work being expended or a precise quantity indicator of vehicle pollution, it is very often an indication that the vehicle is emitting a large amount of unburned hydrocarbons and is in need of maintenance. Preferably, the spectrometer 13 used to identify the contents of the exhaust plume is also capable of identifying at least some emissions 17 which are not part of the visible plume.

Analysis of the emissions content is carried out in processing and computing unit 15 by comparing the measured content with a profile or dynamic model of acceptable emissions for the vehicle in question and its measured weight or load. The data necessary to create such profiles or models is currently available from a number of sources, including the Federal Environmental Protection Agency, and also from vehicle manufacturers and independent testing agencies. Although modifications of the profiles may have to be made in order to take into account the observed ambient conditions, such programming is well within the capabilities of those skilled in the art.

4. Display, Recording, and Alarm Functions and Hardware

Having measured, in real-time, the weight and emissions of a passing vehicle, including an analysis of emissions compliance, and having identified the vehicle, the system is capable of providing the results of the measurements and analysis in a form which is immediately usable by the appropriate enforcement agencies. For example, an audible or visual system alarm or display 18 may be provided which alerts an operator of the system to the non-compliant vehicle and prompts the operator to inform the appropriate authorities, or the enforcement agencies can be directly alerted in real time through a data link 19, allowing them to more quickly apprehend the overweight or polluting vehicle. At the same time, a permanent record of the infraction in the form of a copy of the registration plate of the vehicle taken by high-resolution camera 14 and superimposed with the test results may be stored in a recorder 20. This digital record of each measurement is preferably time-tagged and associated data may be provided with the permanent record for use by enforcement agencies to monitor and analyze traffic factors.

Because of the integrated data collection, the system has the advantage that vehicles with altered or unreadable bar-codes, or vehicles travelling unusually slow or at an excessive speed, can trigger system alarms for investigation or enforcement purposes, and exhaust systems altered to lower the outlet temperature can be identified by the system and an alert generated. While particularly suited to monitoring trucks, the system can also be readily adapted by those skilled in the art to monitor personal automobiles or other vehicles as part of a comprehensive traffic and environmental monitoring and enforcement network.

Those skilled in the art will thus appreciate that numerous variations and modifications of the embodiment described herein are possible within the scope of the invention. The invention provides a non-contact, remote means of measuring the weight of a land vehicle powered by any engine which generates heat and exhaust, burned and unburned, fuel or any combination therein. Examples of such engines include, but are not limited to, gasoline, gasohol, natural gas, propane, diesel, and closed cycle power sources. In addition, the system can be tied to the GPS system to measure the location of the monitoring area and to provide accurate time for time-stamping measurement records. The atmospheric condition measurements can be used as a guide to re-route heavily laden trucks from pollution sensitive areas, and the system may also be used for the detection and reporting of stolen vehicles.

As a result, it is intended that the invention not be construed as being limited in any way by the above description or illustrations, but rather it is intended that the invention be defined solely by the appended claims.

We claim:

1. Apparatus for monitoring the weight and emission compliance of a vehicle, comprising:

a suite of measuring instruments, including:

means connected to a processing and computing device for measuring a velocity of the vehicle travelling on a grade;

means connected to the processing and computing device for detecting a temperature of emissions from the vehicle, said temperature detection means including an infrared thermal imager;

means connected to the processing and computing device for measuring a content of said emissions, said emissions content measuring means including a passive infrared chemical content spectrometer;

means connected to the processing and computing device for identifying the vehicle; and means for measuring ambient weather conditions, including ambient temperature and wind velocity, and wherein the processing and computing device includes:

means for calculating an amount of work performed by said vehicle as it travels along said grade based on the measured temperature of the exhaust, said calculating means including means for factoring into said calculation different grades so as to allow permit the suite to be used at different sites;

means for factoring the measured ambient temperature and wind velocity into the calculation of work performed;

means for determining a weight of the vehicle based at least on the computed work, the measured velocity, grade, and length of the grade;

means for storing vehicle specifications for recall based on identification of the vehicle by the vehicle identification means;

means for recalling from memory data, said data including said vehicle specifications, relating to an acceptable emissions content profile of the vehicle for the calculated weight and velocity;

means for comparing the measured emissions content with the emissions content profile in order to obtain a weight-adjusted emissions measurement.

2. Apparatus as claimed in claim 1, wherein said vehicle identification means comprises means connected to the processing and computing unit for reading a coded decal containing vehicle identification information and attached to the vehicle.

3. Apparatus as claimed in claim 2, wherein said decal has a bar code printed thereon and said reading means is an optical bar code reader.

4. Apparatus as claimed in claim 2, wherein said reading means is an optical character reader.

5. Apparatus as claimed in claim 1, wherein said vehicle identification means includes a transponder on the vehicle and means including an RF code reader connected to the processing and computing unit for reading vehicle identification information transmitted by said transponder.

6. Apparatus as claimed in claim 1, wherein said suite of instruments further includes means for measuring said grade.

7. Apparatus as claimed in claim 1, wherein said means for factoring into said calculation different grades so as to permit the suite to be used at different sites includes means for storing survey data on said grade.

8. Apparatus as claimed in claim 1, wherein said processing and computing device includes means for generating an image of the exhaust from said vehicle based on input from said thermal imager.

9. Apparatus as claimed in claim 1, wherein said emissions content measuring means includes a chemical content spectrometer.

10. Apparatus as claimed in claim 1, further comprising means for alerting users if a vehicle which does not comply with either weight or emissions standards.

11. Apparatus as claimed in claim 1, further comprising means for recording measurements and determinations made by the suite of instruments and by the processing and computing device together with vehicle identification information.

12. Apparatus as claimed in claim 11, wherein said recording means includes a video camera for capturing an image of a registration number of the vehicle.

13. A closed loop system for measuring pollution by a vehicle, comprising:

means including a passive infrared chemical content spectrometer for measuring a pollution content of an exhaust plume emitted by the vehicle;

means including an infrared thermal imager for measuring a temperature of said exhaust plume;

means for storing data concerning vehicle operating characteristics and recalling the data based on identification of the vehicle in order to determine the contribution of weight to an identified vehicle's exhaust plume temperature at a measured velocity and thereby determining a weight of the vehicle;

means for recalling data making up a pollution profile of said vehicle and, based on the determined weight, comparing the measured pollution content with the profile in order to analyze the acceptability of the measured pollution content; and means for sounding an alarm if the pollution content is not acceptable, wherein said weight determining means includes means for measuring ambient weather conditions, including ambient temperature and wind velocity, and for factoring the measured ambient temperature and the measured velocity into a calculation of work performed by the vehicle while travelling along a grade, said work determining means including means for factoring into the weight calculation different grades to permit the system to be used at different sites.

14. A system as claimed in claim 13, wherein said data storage and recalling means includes means for reading a coded decal containing vehicle identification information, and recalling stored specifications for the identified vehicle.

15. A system as claimed in claim 14, wherein said decal has a bar code printed thereon and said data storage and recalling means includes an optical bar code reader.

16. A system as claimed in claim 13, wherein said data storage and recalling means includes an optical character reader.

17. A system as claimed in claim 13, wherein said data storage and recalling means includes a transponder on the vehicle and means including an RF code reader for reading vehicle identification information transmitted by said transponder.

18. A system as claimed in claim 13, further including means for measuring said grade.

19. A system as claimed in claim 13, further including means for recording results of said analysis together with vehicle identification information.

20. A system as claimed in claim 19, wherein said recording means includes a video camera for capturing an image of a registration number of the vehicle.

21. A system as claimed in claim 13, further comprising a data link for transmitting results of said analysis directly to a central enforcement agency.

22. A system for determining the weight of a vehicle, comprising: a suite of measuring instruments, including:

means for identifying a vehicle and storing data concerning vehicle operating characteristics and recalling the data based on identification of the vehicle in order to determine a contribution of weight to an identified vehicle's exhaust plume temperature at a measured velocity;

means for measuring ambient weather conditions, including ambient temperature and wind velocity;

means connected to a processing and computing device for measuring a velocity of the vehicle travelling on a grade;

means for inputting to the processing and Computing device said grade and a length of said grade; and means including a passive infrared thermal imager connected to the processing and computing device for detecting said exhaust plume temperature, wherein the processing and computing device includes:

means for calculating an amount of work performed by said vehicle as it travels along said grade based on the measured temperature of the exhaust plume;

means for determining the weight of the vehicle based at least on the computed work, the measured velocity, grade, length of the grade over which the velocity of the vehicle is monitored, the measured ambient temperature and wind velocity, and stored data concerning vehicle operating characteristics, and ambient weather conditions.

23. A system as claimed in claim 22, wherein said data storage and recalling means includes means for reading a coded decal containing vehicle identification information, and recalling stored specifications for the identified vehicle.

24. A system as claimed in claim 23, wherein said decal includes a bar code and said data storage and recalling means includes an optical bar code reader.

25. A system as claimed in claim 23, wherein said data storage and recalling means includes an optical character reader.

26. A system as claimed in claim 22, wherein said data storage and recalling means includes a transponder on the vehicle and means including an RF code reader for reading vehicle identification information transmitted by said transponder.

27. A method of measuring the emission compliance of a vehicle, comprising the steps of:

identifying the vehicle and retrieving vehicle specifications from a memory based on the vehicle identity;

measuring a velocity of said vehicle as it travels on a grade;

measuring a temperature of an exhaust plume emitted by the vehicle by receiving infrared radiation from the exhaust plume, forming a thermal image of the exhaust plume, and mapping the temperatures within said thermal image;

computing, based on said temperature and on said vehicle specifications, a work output of said vehicle as it travels along said grade;

measuring ambient weather conditions, including ambient temperature and wind velocity, and factoring the measured ambient temperature and wind velocity into the computation of work output;

computing, from said work output and said measured velocity, a weight of said vehicle;

measuring the actual pollution content of the exhaust plume by performing a chemical content spectrographic analysis of the exhaust plume;

retrieving, for a vehicle having the computed weight and travelling at the measured velocity, emissions profile data stored in a memory and analyzing the emissions compliance of said exhaust plume based on a comparison between said retrieved emissions profile data profile and said measured exhaust plume pollution content; and alerting a user to results of the analysis.

28. A method as claimed in claim 27, wherein the step of identifying the vehicle comprises the step of reading a coded decal containing vehicle identification information and attached to the vehicle.

29. A method as claimed in claim 28, wherein the step of reading the coded decal includes the step of optically reading the coded decal.

30. A method as claimed in claim 27, wherein the step of identifying the vehicle comprises the step of receiving RF signals from a transponder on the vehicle.

31. A method as claimed in claim 27, further comprising the step of alerting authorities to a vehicle which does not comply with either weight or emissions standards.

32. A method as claimed in claim 27, further comprising the step of recording results of the analysis together with vehicle identification information.

33. A method as claimed in claim 32, wherein said recording step includes the step of capturing a video image of a registration number of the vehicle.

34. A method of measuring pollution by a vehicle, comprising the steps of:

measuring a pollution content of an exhaust plume emitted by the vehicle by performing a chemical content spectrographic analysis of the exhaust plume;

determining a weight of the vehicle by measuring a velocity of the vehicle as it travels on an upgrade, measuring a temperature of the exhaust plume, measuring ambient weather conditions including ambient temperature and wind velocity, and retrieving data concerning vehicle operating characteristics from a memory based on identification of the vehicle in order to determine a contribution of weight to an identified vehicle's exhaust plume temperature at the measured velocity;

retrieving from a memory data making up a pollution profile of said vehicle, based on the determined weight, comparing the measured pollution content with the profile in order to analyze the acceptability of the measured pollution content; and sounding an alarm if the pollution content is not acceptable, wherein the step of measuring the temperature of the exhaust plume comprises the step of detecting infrared radiation from said exhaust plume, forming a thermal image of the exhaust plume, and mapping the temperature within said thermal image.

35. A method as claimed in claim 34, wherein said data storage and retrieving step includes the step of reading a coded decal containing vehicle identification information, and retrieving from the memory stored specifications for the identified vehicle.

36. A method as claimed in claim 34, wherein said data storage and retrieving step includes the step of receiving RF coded data from a transponder on the vehicle.

37. A method as claimed in claim 34, further including the step of recording results of said analysis together with vehicle identification information.

38. A method as claimed in claim 34, further comprising the step of transmitting results of said analysis directly to a central enforcement agency via a data-link.

39. A method of remotely determining the weight of a vehicle without contacting the vehicle, comprising the steps of:

identifying the vehicle and retrieving from memory vehicle specification based on the vehicle identity;

measuring ambient weather conditions, including ambient temperature and wind velocity;

measuring a velocity of said vehicle as it travels on a grade;

means for inputting said grading and length of grade to a processing means so that the method can be applied at different sites;

measuring a temperature of an exhaust plume emitted by the vehicle by receiving infrared radiation from the exhaust plume, forming a thermal image of the exhaust plume, and mapping temperatures within said thermal image;

computing, based on said exhaust plume temperature, vehicle specifications, and measured ambient temperature and wind velocity, input grade and length of grade; and computing, from said work output and said measured velocity, the weight of said vehicle.

40. A method as claimed in claim 39, wherein the step of identifying the vehicle comprises the step of reading a coded decal containing vehicle identification information and attached to the vehicle.

41. A method as claimed in claim 40, wherein the step of reading the coded decal includes the step of optically reading the coded decal.

42. A method as claimed in claim 39, wherein the step of identifying the vehicle comprises the step of receiving RF signals from a transponder on the vehicle.

43. A method as claimed in claim 39, further comprising the step of alerting authorities to a vehicle which does not comply with weight standards.

44. A method as claimed in claim 39, further comprising the step of recording results of the analysis together with vehicle identification information.

* * * * *

UNITED STATES PATENT AND TRADEMARK OFFICE
CERTIFICATE OF CORRECTION

PATENT NO. : 5,583,765
DATED : August 23, 1994
INVENTOR(S) : Kleehammer et al

It is certified that error appears in the above-indentified patent and that said Letters Patent is hereby corrected as shown below:

On the title page: Item [75] Inventors: add "Stanley M. Reich, Jericho, NY. and Thomas Reilly, Hauppauge, NY"

Signed and Sealed this

Twenty-second Day of July, 1997

BRUCE LEHMAN

*Attest:*

*Attesting Officer*  Commissioner of Patents and Trademarks